United States Patent
Ichim et al.

(10) Patent No.: US 11,795,433 B2
(45) Date of Patent: Oct. 24, 2023

(54) GENERATION OF AUTOLOGOUS IMMUNE MODULATORY CELLS FOR TREATMENT OF NEUROLOGICAL CONDITIONS

(71) Applicant: Creative Medical Technologies, Inc., Phoenix, AZ (US)

(72) Inventors: Thomas Ichim, San Diego, CA (US); Amit Patel, Salt Lake City, UT (US)

(73) Assignee: Creative Medical Technologies, Inc, Phoenix, AZ (US)

( * ) Notice: Subject to any disclaimer, the term of this patent is extended or adjusted under 35 U.S.C. 154(b) by 0 days.

(21) Appl. No.: 15/987,739

(22) Filed: May 23, 2018

(65) Prior Publication Data

US 2018/0340145 A1    Nov. 29, 2018

Related U.S. Application Data

(60) Provisional application No. 62/510,203, filed on May 23, 2017.

(51) Int. Cl.
  *C12N 5/073*     (2010.01)
  *C12N 5/078*     (2010.01)

(52) U.S. Cl.
  CPC ......... *C12N 5/0605* (2013.01); *C12N 5/0634* (2013.01); *C12N 2501/01* (2013.01); *C12N 2501/115* (2013.01); *C12N 2501/13* (2013.01); *C12N 2501/2302* (2013.01); *C12N 2502/025* (2013.01); *C12N 2502/11* (2013.01); *C12N 2533/50* (2013.01)

(58) Field of Classification Search
  CPC ................ C12N 5/0605; C12N 5/0634; C12N 2502/11; C12N 2502/025
  See application file for complete search history.

(56) References Cited

U.S. PATENT DOCUMENTS

| | | | |
|---|---|---|---|
| 6,281,012 B1 * | 8/2001 | McIntosh | C12N 5/0637 435/372 |
| 2007/0122903 A1 * | 5/2007 | Rezania | A61P 3/10 435/325 |

OTHER PUBLICATIONS

Moorefield et al., Cloned, CD117 selected human amniotic fluid stem cells are capable of modulating the immune response. PLoS One, vol. 6, No. 10 (2011) e26535. (Year: 2011).*

Mareschi et al., Immunoregulatory effects on T lymphocytes by human mesenchymal stromal cells isolated from bone marrow, amniotic fluid, and placenta. Experimental Hematology, vol. 44, No. 2 (Feb. 2016) pp. 138-150. (Year: 2016).*

Wang et al., The allogeneic umbilical cord mesenchymal stem cells regulate the function of T helper 17 cells from patients with rheumatoid arthritis in an in vitro co-culture system. BMC Musculoskeletal Disorders, vol. 13 (2012) article 49. (Year: 2012).*

Roubelakis et al., Molecular and proteomic characterization of human mesenchymal stem cells derived from amniotic fluid: Comparison to bone marrow mesenchymal stem cells. Stem Cells and Development, vol. 16, No. 6 (Dec. 2007) pp. 869-1059 (Year: 2007).*

* cited by examiner

*Primary Examiner* — Kara D Johnson
(74) *Attorney, Agent, or Firm* — Baumgartner Patent Law; Marc Baumgartner

(57) ABSTRACT

Disclosed are means, methods, and compositions of matter useful for treatment of neuroinflammation, autoimmunity, transplant rejection, or graft versus host disease (GVHD) comprising exposing autologous immune cells to allogeneic amniotic fluid derived stem cells. In one embodiment peripheral blood mononuclear cells are cultured in the presence of amniotic fluid stem cells in the presence of interleukin-2 for a period of time sufficient to endow tolerogenic properties. Said tolerogenic properties include ability to suppress adaptive or innate immune responses. In another embodiment the invention provides methods of generating antigen specific immune regulatory cells by culture of lymphocytes together with amniotic fluid stem cells in the presence of antigen to which specific immune regulation is desired.

5 Claims, 1 Drawing Sheet

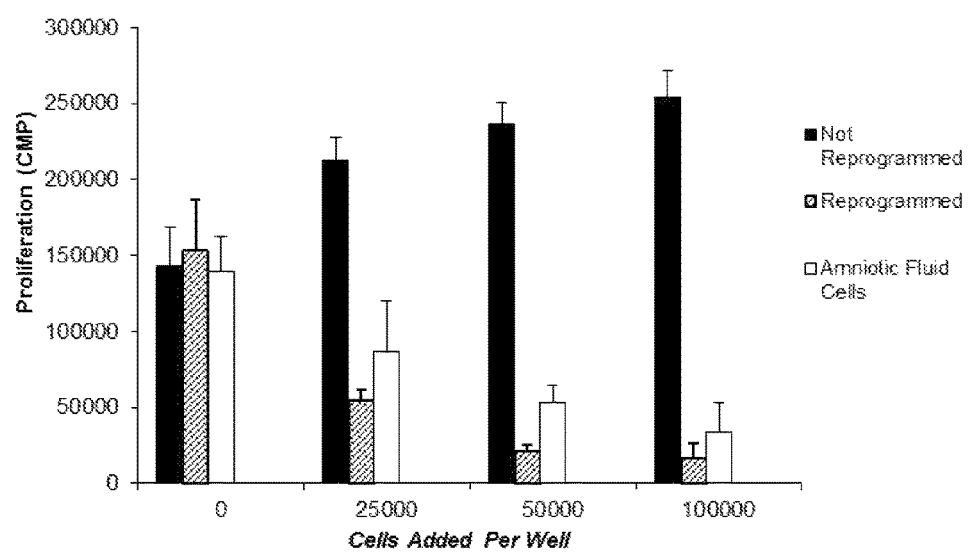

GENERATION OF AUTOLOGOUS IMMUNE MODULATORY CELLS FOR TREATMENT OF NEUROLOGICAL CONDITIONS

CROSS-REFERENCE TO RELATED APPLICATIONS

This application is related to, and claims the benefit of, U.S. Provisional Application No. 62/510,203, filed May 23, 2017. The above-identified priority application is incorporated herein by reference in its entirety.

FIELD OF THE INVENTION

The invention relates to the area of immune modulation, more specifically the invention relates to the use of mesenchymal stem cells for expansion of immune regulator cells, more specifically, the invention relates to the utilization of allogeneic mesenchymal stem cells for stimulation of autologous immune regulatory cells. More specifically, the invention relates to the use of amniotic fluid stem cells for expansion of autologous immune regulatory cells.

BACKGROUND

Immune modulatory cells are useful for the treatment of medical conditions, such as ischemic neurological conditions, for example. The prior art includes challenges to the expansion of immune regulator cells. Accordingly there is a need in the art for improved methods of expanding immune regulator cells.

SUMMARY

Embodiments herein are directed to methods of generating immune modulatory cells comprising the steps of: a) obtaining an allogeneic amniotic fluid stem cell population; b) culturing said allogeneic amniotic fluid stem cell population with autologous immune cells; and c) extracting cells from said tissue culture which have been endowed with immune modulatory properties.

BRIEF DESCRIPTION OF THE DRAWINGS

FIG. 1 is a bar graph showing the CPM (counts per minute) readout of proliferation in the MLR of the reprogrammed PMBCs, non-reprogrammed PMBCs, and amniotic fluid stem cells.

DETAILED DESCRIPTION OF THE INVENTION

The invention provides means of expanding immune modulatory cells using amniotic fluid stem cells. In one embodiment of the invention, amniotic stem cells are grown together with peripheral blood mononuclear cells in a culture containing a 1:1 ratio. Culture is performed for 7 days in the presence of IL-2 at 35 ng per ml. After culture, nonadherent cells are extracted and administered to a patient suffering from an inflammatory condition, more specifically from a neuroinflammatory condition.

The invention teaches the use of cells derived from amniotic fluid for expansion of immune modulatory cells useful for the treatment of ischemic neurological conditions. The cells described in the invention are immortal in culture, maintain cuploidy for >1 year in culture, share markers with human ES cells, and are capable of differentiating into all three germ layers of the developing embryo, Endoderm, Mesoderm and Ectoderm. In a preferred embodiment the regenerative amniotic fluid cells are found in the amnion harvested during the second trimester of human pregnancies. It is known that amniotic fluid contains multiple morphologically-distinguishable cell types, the majority of the cells are prone to senescence and are lost from cultures. In one embodiment, fibronectin coated plates and culture conditions described in U.S. Pat. No. 7,569,385 are used to grow cells from amniotic fluid harvests from normal 16-18 week pregnancies. The cells of the invention are of fetal origin, and have a normal diploid karyotype. Growth of the amniotic fluid stem cells as described in the invention for use in neurological ischemic conditions results in cells that are multipotent, as several main cell types have been derived from them. As used herein, the term "multipotent" refers to the ability of amniotic fluid regenerative cells to differentiate into several main cell types. The MAFSC cells may also be propagated under specific conditions to become "pluripotent." The term "pluripotent stem cells" describes stem cells that are capable of differentiating into any type of body cell, when cultured under conditions that give rise to the particular cell type. The Amniotic fluid regenerative cells are preferably isolated from humans. However, the Amniotic fluid regenerative cells may be isolated in a similar manner from other species. Examples of species that may be used to derive the Amniotic fluid regenerative cells include but are not limited to mammals, humans, primates, dogs, cats, goats, elephants, endangered species, cattle, horses, pigs, mice, rabbits, and the like.

The amniotic fluid-derived cells and MAFSC can be recognized by their specific cell surface proteins or by the presence of specific cellular proteins. Typically, specific cell types have specific cell surface proteins. These surface proteins can be used as "markers" to determine or confirm specific cell types. Typically, these surface markers can be visualized using antibody-based technology or other detection methods. One method of characterizing cellular markers is FACS analysis.

The surface markers of isolated MAFSC cells derived from independently-harvested amniotic fluid samples can be tested for a range of cell surface and other markers, using monoclonal antibodies and FACS analysis. These cells can be characterized by the following cell surface markers: SSEA3, SSEA4, Tra-1-60, Tra-1-81, Tra-2-54. The MAFSC cells can be distinguished from mouse ES cells in that the MAFSC cells do not express the cell surface marker SSEA1. Additionally, MAFSC express the stem cell transcription factor Oct-4. The MAFSC cells can be recognized by the presence of at least one, or at least two, or at least three, or at least four, or at least five, or at least six, or all of the following cellular markers SSEA3, SSEA4, Tra-1-60, Tra-1-81, Tra-2-54 and Oct-4.

In some embodiments of the present invention, the SSEA3 marker is expressed in a range of from about 90%, 92%, 94% to about 96%, 98%, 99%, or 100% of the cells in the MAFSC culture. The SSEA4 marker can be expressed, for example, in a range of from about 90%, 92%, 94% to about 96%, 98%, 99%, or 100% of the cells in the MAFSC culture. In some embodiments of the present invention, the Tra-1-60 marker expressed, for example, in a range of from about 60%, 65%, or 70% to about 85%, 90%, or 95% of the cells in the MAFSC culture. In some embodiments of the present invention, the Tra-1-81 marker is expressed in a range of from about 70%, 75%, or 80% to about 85%, 90%, or 95% of the cells in the MAFSC culture. The Tra-2-84 marker can be expressed, for example, in a range of from about 55%, 60%, 65%, or 70% to about 80%, 90%, or 95% of the cells in the MAFSC culture. In some embodiments of the present invention, the Oct-4 marker is expressed in a range of from about 25%, 30%, 35%, or 40% to about 45%, 55%, 65%, or 70% of the cells in the MAFSC culture.

The MAFSC cultures express very little or no SSEA-1 marker. In addition to the embryo stem cell markers SSEA3, SSEA4, Tra1-60, Tra1-81, Tra2-54, Oct-4 the amniotic fluid regenerative cells also expressed high levels of the cell surface antigens that are normally found on human mesenchymal stem cells, but not normally on human embryo stem cells (M F Pittinger et al., Science 284:143-147, 1999; S Gronthos et al., J. Cell Physiol. 189:54-63, 2001). This set of markers includes CD13 (99.6%) aminopeptidase N, CD44 (99.7%) hyaluronic acid-binding receptor, CD49b (99.8%) collagen/laminin-binding integrin alpha2, and CD105 (97%) endoglin. The presence of both the embryonic stem cell markers and the hMSC markers on the MAFSC cell cultures indicates that amniotic fluid-derived MAFSC cells, grown and propagated as described here, represent a novel class of human stem cells that combined the characteristics of hES cells and of hMSC cells.

In some embodiments of the invention, at least about 90%, 94%, 97%, 99%, or 100% of the cells in the culture express CD13. In additional embodiments, at least about 90%, 94%, 97%, 99%, or 100% of the cells in the culture express CD44. In some embodiments of the invention, a range from at least about 90%, 94%, 97%, 99%, 99.5%, or 100% of the cells in the culture express CD49b. In further embodiments of the invention, a range from at least about 90%, 94%, 97%, 99%, 99.5%, or 100% of the cells in the culture express CD105.

In a particularly advantageous embodiment, the amniotic fluid regenerative cells are human stem cells that can be propagated for an indefinite period of time in continuous culture in an undifferentiated state. The term "undifferentiated" refers to cells that have not become specialized cell types. A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors.

The cells may also be "banked" or stored in a manner that allows the cells to be revived as needed in the future, an aliquot of the undifferentiated cells can be removed at any time, to be differentiated into a particular cell type or tissue type, and may then be used to treat a disease or to replace malfunctioning tissues in a patient. Since the cells are harvested from the amniotic fluid, the cells can be stored so that an individual can have access to his or her own undifferentiated cells for an entire lifetime.

The Amniotic fluid regenerative cells may be grown in an undifferentiated state for as long as desired (and optionally stored as described above), and can then be cultured under certain conditions to allow progression to a differentiated state. By "differentiation" is meant the process whereby an unspecialized cell acquires the features of a specialized cell such as a heart, liver, muscle, pancreas or other organ or tissue cell. The Amniotic fluid regenerative cells, when cultured under certain conditions, have the ability to differentiate in a regulated manner into three or more subphenotypes. Once sufficient cellular mass is achieved, cells can be differentiated into endodermal, mesodermal and ectodermal derived tissues in vitro and in vivo. This planned, specialized differentiation from undifferentiated cells towards a specific cell type or tissue type is termed "directed differentiation."

Exemplary cell types that may be prepared from Amniotic fluid regenerative cells using directed differentiation include but are not limited to fat cells, cardiac muscle cells, epithelial cells, liver cells, brain cells, blood cells, neurons, glial cells, pancreatic cells, and the like.

There are several types of amniotic fluid stem cells that are useful for the practice of the invention. These including conventionally isolated cells [1-3], as well as cells selected based on expression of CD117, otherwise known as c-kit [4, 5].

In one embodiment of the invention, cells that are used are $CD117^{pos}$ AFS cells that represent a subpopulation of fetal SCs expressing the type III-tyrosine kinase receptor of the stem cell factor (c-kit), and are considered as excellent candidates for the SC based-approaches in regenerative medicine. AFS cells display some multipotent mesenchymal stromal cell (MSC) markers, such as CD73, CD90, and CD105 and some pluripotency-associated markers, such as Oct4 and NANOG and the stage-specific embryonic antigen (SSEA-4). Although AFS cells have been shown to differentiate in vitro toward cell lineages deriving from the three germ layers, including adipose, osteoblastic, myogenic, endothelial, neuronal, and hepatic cells, these properties were not unequivocally confirmed in vivo; moreover, AFS cells do not induce teratoma formation when injected into mice. Both first and second trimester-derived AFS cells revert to a functional pluripotent state when cultured in small molecule cocktail, that is, chemically induced pluripotent stem cells. Furthermore, AFS cells cross the endothelial barrier after systemic injection, thus engrafting into injured tissues. The therapeutic efficacy of AFS cells has been recently verified in in vivo preclinical studies showing their capabilities to regenerate and improve the functionality of injured tissues and to restore cell niche homeostasis in muscle, bone, lung, and kidney.

Example 1

Superior Immune Modulation by Peripheral Blood Mononuclear Cells Reprogrammed by Culture with Amniotic Fluid Stem Cells Amniotic fluid stem cells were generated by culture of amniotic fluid as described in the specification. A 7 day coculture at a 1:1 ratio was performed with peripheral blood mononuclear cells that were allogeneic to the amniotic fluid stem cells. Media was supplemented with 35 ng/ml of IL-2. Subsequent to culture, non-adherent PBMC were removed and added to an ongoing mixed lymphocyte reaction which was established by culture of 100,000 PBMC from one donor and another 100,000 PBMC from another donor. It was found that naïve PBMC induced a mild stimulation of the MLR, whereas reprogrammed PBMC were superior at inhibiting MLR compared to amniotic fluid stem cells. FIG. 1 is a bar graph showing the CPM (counts per minute) readout of proliferation in the MLR of the reprogrammed PMBCs, non-reprogrammed PMBCs, and amniotic fluid stem cells.

REFERENCES

1. Prusa, A. R., et al., *Oct-4-expressing cells in human amniotic fluid: a new source for stem cell research?* Hum Reprod, 2003. 18(7): p. 1489-93.
2. Karlmark, K. R., et al., *Activation of ectopic Oct-4 and Rex-1 promoters in human amniotic fluid cells*. Int J Mol Med, 2005. 16(6): p. 987-92.

3. Tsai, M. S., et al., *Clonal amniotic fluid-derived stem cells express characteristics of both mesenchymal and neural stem cells.* Biol Reprod, 2006. 74(3): p. 545-51.
4. De Coppi, P., et al., *Isolation of amniotic stem cell lines with potential for therapy.* Nat Biotechnol, 2007. 25(1): p. 100-6.
5. Pozzobon, M., et al., *Isolation of c-Kit+ human amniotic fluid stem cells from second trimester.* Methods Mol Biol, 2013. 1035: p. 191-8.

The invention claimed is:

1. A method of generating cells having immune suppression properties comprising: a) harvesting amniotic fluid; b) centrifuging the amniotic fluid to separate an amniotic stem cell population; c) plating said amniotic stem cell population onto plates coated with fibronectin, and culturing in medium and with 2% serum; d) selecting and separating a mesenchymal stem cell population from said amniotic stem cell population which adhere to the plates; e) culturing said adherent mesenchymal stem cell population with a population of allogeneic peripheral blood mononuclear cells at a 1:1 ratio and; f) isolating a cell population consisting essentially of: mortal, non-adherent peripheral blood mononuclear cells having immune suppression properties from said culture of adherent mesenchymal stem cell population and said population of peripheral blood mononuclear cells.

2. The method of claim 1, wherein said mortal, non-adherent peripheral blood mononuclear cells possess ability to inhibit secretion of inflammatory cytokines.

3. The method of claim 2, wherein said inflammatory cytokines are selected from the group consisting of; a) IFN-gamma (interferon-gamma); b) TNF-alpha (tumor necrosis factor-alpha); c) IL-2 (interleukin-2); d) IL-7 (interleukin-7); e) IL-12 (interleukin-12); IL-15 (interleukin-15); g) IL-17 (interleukin-17); h) IL-18 (interleukin-18); i) IL-21 (interleukin-21); j) IL-23 (interleukin-23); k) IL-27 (interleukin-27); l) IL-33 (interleukin-33); m) HMGB-1 (high mobility group box 1); and n) TRAIL (tumor necrosis factor-related apoptosis-inducing ligand).

4. The method of claim 1, wherein said adherent amniotic fluid stem cell population is maintained in an undifferentiated state during said culture with said population of allogeneic peripheral blood mononuclear cells.

5. The method of claim 1, wherein said adherent amniotic fluid stem cell population is further cultured in the presence of a substance selected from the group consisting of: nerve growth factor, bFGF (basic fibroblast growth factor), dibutryl cAMP (dibutryl cyclic adenosine monophosphate), IBMX (3-isobutyl-1-methylxanthine), and retinoic acid for four weeks.

* * * * *